United States Patent
Maynard et al.

(10) Patent No.: US 12,201,766 B2
(45) Date of Patent: *Jan. 21, 2025

(54) DRY POWDER NEBULIZER

(71) Applicant: UNM Rainforest Innovations, Albuquerque, NM (US)

(72) Inventors: Nicola Jeanne Maynard, Albuquerque, NM (US); Hugh D. C. Smyth, Austin, TX (US)

(73) Assignee: UNM Rainforest Innovations, Albuquerque, NM (US)

( * ) Notice: Subject to any disclaimer, the term of this patent is extended or adjusted under 35 U.S.C. 154(b) by 79 days.

This patent is subject to a terminal disclaimer.

(21) Appl. No.: 18/099,011

(22) Filed: Jan. 19, 2023

(65) Prior Publication Data
US 2023/0293832 A1    Sep. 21, 2023

Related U.S. Application Data

(63) Continuation of application No. 16/892,900, filed on Jun. 4, 2020, now Pat. No. 11,571,528, which is a
(Continued)

(51) Int. Cl.
*A61M 15/00* (2006.01)
*A61M 11/00* (2006.01)
*A61M 16/00* (2006.01)

(52) U.S. Cl.
CPC ...... *A61M 15/0086* (2013.01); *A61M 11/003* (2014.02); *A61M 15/00* (2013.01);
(Continued)

(58) Field of Classification Search
CPC ............ A61M 15/0086; A61M 11/003; A61M 15/0006; A61M 15/0021; A61M 15/003;
(Continued)

(56) References Cited

U.S. PATENT DOCUMENTS

| | | |
|---|---|---|
| 5,080,093 A | 1/1992 | Raabe et al. |
| 5,785,245 A | 7/1998 | Tedders, Jr. et al. |

(Continued)

FOREIGN PATENT DOCUMENTS

WO    WO-2011112531 A2    9/2011

OTHER PUBLICATIONS

"U.S. Appl. No. 13/583,606, Notice of Allowance mailed Feb. 23, 2015", 9 pgs.
(Continued)

*Primary Examiner* — Steven O Douglas
(74) *Attorney, Agent, or Firm* — Schwegman Lungber & Woessner, P.A.

(57) ABSTRACT

A dry powder delivery device may be configured to provide micronized dry powder particles to airways of a user. The device may include a cylindrical container delimiting a chamber containing at least one magnetically-responsive object, a motor external to said chamber, a magnet external to the chamber and rotatably coupled with the motor, and an outflow member configured to direct airflow to a user. The magnetically-responsive object may be coated with micronized dry powder particles, and the motor may be operable to rotate the magnet about an axis. Rotation of the magnet creates a magnetic field that causes the magnetically-responsive object to move in response to the magnetic field and collide with a side wall of the container to deaggregate the dry powder particles and aerosolize the dry powder in the chamber.

20 Claims, 4 Drawing Sheets

Related U.S. Application Data continuation of application No. 15/676,705, filed on Aug. 14, 2017, now Pat. No. 10,702,664, which is a continuation of application No. 14/739,738, filed on Jun. 15, 2015, now Pat. No. 9,731,088, which is a continuation of application No. 13/583,606, filed as application No. PCT/US2011/027465 on Mar. 8, 2011, now Pat. No. 9,078,985.

(60) Provisional application No. 61/456,812, filed on Nov. 12, 2010, provisional application No. 61/311,707, filed on Mar. 8, 2010.

(52) U.S. Cl.
CPC .... *A61M 15/0006* (2014.02); *A61M 15/0021* (2014.02); *A61M 15/003* (2014.02); *A61M 15/0035* (2014.02); *A61M 15/009* (2013.01); *A61M 2016/0015* (2013.01); *A61M 2202/064* (2013.01); *A61M 2205/0272* (2013.01); *A61M 2205/8287* (2013.01); *A61M 2206/16* (2013.01)

(58) Field of Classification Search
CPC .............. A61M 15/0035; A61M 15/00; A61M 15/009; A61M 2016/0015; A61M 2202/064; A61M 2205/0272; A61M 2205/8287; A61M 2206/16
See application file for complete search history.

(56) References Cited

U.S. PATENT DOCUMENTS

| | | |
|---|---|---|
| 6,976,647 B2 | 12/2005 | Reed et al. |
| 8,381,780 B2 | 2/2013 | Fisher et al. |
| 8,684,284 B2 | 4/2014 | Harutyunyan |
| 9,078,985 B2 | 7/2015 | Maynard et al. |
| 9,731,088 B2 | 8/2017 | Maynard et al. |
| 10,702,664 B2 | 7/2020 | Maynard et al. |
| 2003/0015197 A1 | 1/2003 | Hale et al. |
| 2008/0068920 A1 | 3/2008 | Galliher et al. |
| 2008/0223364 A1 | 9/2008 | Hickey et al. |
| 2009/0071473 A1 | 3/2009 | Abrams |
| 2013/0000640 A1 | 1/2013 | Maynard et al. |
| 2014/0020684 A1 | 1/2014 | Klasek et al. |
| 2015/0343158 A1 | 12/2015 | Maynard et al. |
| 2017/0340845 A1 | 11/2017 | Maynard et al. |
| 2020/0368461 A1 | 11/2020 | Maynard et al. |

OTHER PUBLICATIONS

"U.S. Appl. No. 13/583,606, PTO Response to Rule 312 Communication mailed Jun. 12, 2015", 2 pgs.

"U.S. Appl. No. 14/739,738, Non Final Office Action mailed Sep. 22, 2016", 7 pgs.

"U.S. Appl. No. 14/739,738, Notice of Allowance mailed Apr. 12, 2017", 7 pgs.

"U.S. Appl. No. 14/739,738, Preliminary Amendment filed Aug. 20, 2015", 5 pgs.

"U.S. Appl. No. 14/739,738, Response filed Jan. 23, 2017 to Non-Final Office Action mailed Sep. 22, 2016", 7 pgs.

"U.S. Appl. No. 15/676,705 Response filed Dec. 10, 2019 to Non Final Office Action mailed Oct. 1, 2019", 7 pgs.

"U.S. Appl. No. 15/676,705, Corrected Notice of Allowability mailed Apr. 22, 2020", 2 pgs.

"U.S. Appl. No. 15/676,705, Non Final Office Action mailed Oct. 1, 2019", 6 pgs.

"U.S. Appl. No. 15/676,705, Notice of Allowance mailed Feb. 27, 2020", 5 pgs.

"U.S. Appl. No. 15/676,705, Preliminary Amendment filed Aug. 15, 2017", 6 pgs.

"U.S. Appl. No. 16/892,900, Non Final Office Action mailed Jun. 22, 2022", 7 pgs.

"U.S. Appl. No. 16/892,900, Notice of Allowance mailed Oct. 4, 2022", 5 pgs.

"U.S. Appl. No. 16/892,900, Preliminary Amendment filed Aug. 14, 2020", 6 pgs.

"U.S. Appl. No. 16/892,900, Response filed Sep. 8, 2022 to Non Final Office Action mailed Jun. 22, 2022", 6 pgs.

"International Application Serial No. PCT/US2011/027465, International Preliminary Report on Patentability mailed Sep. 20, 2012", 7 pgs.

"International Application Serial No. PCT/US2011/027465, International Search Report mailed Nov. 14, 2011", 9 pgs.

"International Application Serial No. PCT/US2011/027465, Writen Opinion mailed Nov. 14, 2011", 5 pgs.

DRY POWDER NEBULIZER

CROSS-REFERENCE TO RELATED APPLICATIONS

This application is a continuation of U.S. application Ser. No. 16/892,900, filed Jun. 4, 2020, which is a continuation of U.S. application Ser. No. 15/676,705, filed Aug. 14, 2017, which is a continuation of U.S. application Ser. No. 14/739,738, filed Jun. 15, 2015, which is a continuation of U.S. application Ser. No. 13/583,606, filed Sep. 7, 2012, which application is a U.S. National Stage Filing under 35 U.S.C. 371 from International Application No. PCT/US2011/027465, filed on Mar. 8, 2011, and published as WO 2011/112531 on Sep. 15, 2011, which claims the benefit of priority of U.S. provisional application No. 61/311,707, entitled "Dry Powder Nebulizer," filed on Mar. 8, 2010, and U.S. provisional application No. 61/456,812, entitled "Dry Powder Nebulizer," filed on Nov. 12, 2010, the contents of all of which are incorporated herein by reference.

TECHNICAL FIELD

The present disclosure relates to systems and methods of delivering micronized dry powder particles to the airways of a patient and, more particularly, a dry powder nebulizer and method for delivering micronized drug powder particles to the deep lung of a patient.

BACKGROUND

Technological advancement in the context of targeted drug delivery to the lung continues to be an emerging field. The ability to deliver therapeutic agents specifically to the lung has been popular in the treatment of specific disease states such as asthma, chronic obstructive pulmonary disease (COPD), infections, cancer, and others. Given its extremely large surface area, mild environment, and ease of administration, in contrast to oral and intravenous routes of drug delivery, the lung presents an especially attractive avenue of therapeutic delivery.

However, pulmonary drug delivery is not without its obstacles. For drug particles to deposit in the deep lung, where they exert their therapeutic action, they must possess certain physical properties. Specifically, the drug particles must have an aerodynamic diameter below 5 microns, where the aerodynamic diameter encompasses both the density and geometric diameter of the drug particle. Accordingly, aerosolized drug particles must be less than 5 microns in aerodynamic diameter when they exit an inhaler to deposit in the deep lung.

The majority of devices for targeted drug delivery to the lung can be categorized into one of three groups: metered dose inhalers (MDI), dry powdered inhalers (DPI), and nebulizers. Researchers have advanced each technology to more adequately fit the needs of prescribers, patients, and even environmentalists concerned with the release of ozone-depleting propellants. While many of the devices currently utilized in theory deliver a set dose, patient variables such as inspiratory capacity and coordination alter the performance and thus therapeutic effect achieved through the use of the device. Most devices however, deliver only small quantities of drug per dose or take long periods of time to deliver a clinically relevant dose in many diseases.

Metered-dose inhalers consist of a small device which contains a formulation of drug particles suspended in a liquid. Typically the doses delivered by these inhalers are small, in the microgram range, often too small for many clinical applications. The patient can then actuate the device to receive a set, metered, dose. Although these devices do not require a significant inspiratory capacity (30 L/min, e.g.), they do require the patient to have been properly counseled and demonstrate consistent coordination to receive the intended manufacturers' dose. Although spacers and other devices have been developed to circumvent this problem, many patients continue to inappropriately utilize their devices, compromising the effectiveness of their medication and leading to poorer and unpredictable patient outcomes. Formulation problems such as the inability to include drugs not stable in a liquid environment and a limited shelf-life are also major challenges. Further, propellants which used to be included in many formulations to assist in the delivery process, such as chlorofluorocarbons (CFCs), have been suspect in the depletion of the ozone layer and manufacturers have been required to reformulate their products to contain non-hazardous materials. This change has led to patients having to change their products, which are potentially more expensive and inconsistent in therapeutic efficacy.

Traditional nebulizers are also liquid formulations of drugs which are delivered to patients who cannot physically actuate or coordinate MDIs or DPIs, primarily young children and the very ill. They carry many of the same formulation and stability problems as MDIs and additionally are inefficient, bulky, and require the patient to breathe the contents over lengthy periods of time (15-30 minutes) due to the need to dissolve or finely disperse the drug within an aqueous liquid. As many medications used to treat disease states are prescribed to be taken several times a day, using nebulizers remain an inconvenience to patients and caretakers particularly due to these long treatment times.

Dry powdered inhalers can be broken down into two subcategories, passive and active devices. DPIs are formulations of dry powders which are administered at set doses. Currently, the majority of DPIs on the market are passive, meaning they are designed to deliver their intended dose when the patient has demonstrated a significant inspiratory capacity (60 L/min, e.g.) needed to mobilize the powders. Although DPIs are free from many of the issues and concerns that restrict MDIs and nebulizers (such as formulation, stability, coordination, and hazardous complications), their performance, and corresponding drug delivery, can be drastically impaired if the patient is unable to inspire at the tested rate; common in COPD, asthma, and pediatric populations. This, again, can lead to unpredictable and unfavorable patient outcomes if used incorrectly. For example, DPI's currently on the market are inadequate because they are liquid formulations, which result in instability, incompatibility, a requirement of advanced coordination, and provide erratic delivery, which in heightened with improper use. Furthermore, the current dry powder formulations have limited delivery and require large inspiratory force, adversely affecting the sick, elderly, and children. This has shown to be problematic for patient populations who have diminished lung function resulting from advanced age or the disease process itself. These populations might experience more therapeutic failures and adverse effects related to the drug due to inability to generate a dispersion patter reflective of those seen in clinical trials.

In an attempt to mitigate this unpredictability, research groups have focused on developing active devices. Active devices utilize a power source to decrease the need for the patient to inspire at the typical DPI requirement, however, many of these devices have not yet come to market and may demonstrate some dosing inconsistencies when used at different patient inspiratory flow rates. In addition, many devices are exceedingly complicated in design and manufacture, adding time and cost to the development of therapies. DPIs can deliver a wide range of doses from low micrograms to milligrams. Having the drug in the solid state enables higher payloads than if the drug needs to be dispersed or dissolved in a solvent. However, as the doses increase, generally performance decreases.

Another caveat for targeted drug therapy is payload capabilities. When considering drug classes such as aminoglycosides and fluoroquinolones, the effectiveness of therapy is dependent on the amount of drug exposed to the site of interest.

It may be desirable to provide a drug delivery device incorporating many of the beneficial qualities of the above MDI, DPI, and nebulizer devices as well as additional features which have the potential to benefit several disease states, unique from the other devices currently on the market. It may be desirable to provide consistency in the delivery of relatively large doses and intermediate doses under conditions which model inter- and intra-patient variability have historically created problems in the performance for standard devices. It may be desirable to provide a device that offers high doses and excellent performance at various flow rates and various orientations (as patients will position the device differently each time they use) and aesthetic appeal. Finally, it may be desirable that the device is simple and cost minimized.

SUMMARY OF INVENTION

According to various aspects of the disclosure, a dry powder delivery device may be configured to provide micronized dry powder particles to airways of a user. The device may include a cylindrical container delimiting a chamber containing at least one magnetically-responsive object, a motor external to said chamber, a magnet external to the chamber and rotatably coupled with the motor, and an outflow member configured to direct airflow to a user. The magnetically-responsive object may be coated with micronized dry powder particles, and the motor may be operable to rotate the magnet about an axis. Rotation of the magnet creates a magnetic field that causes the magnetically-responsive object to move in response to the magnetic field and collide with a side wall of the container to deaggregate the dry powder particles and aerosolize the dry powder in the chamber.

According to some aspects, the magnetically-responsive object may comprise a magnet such as, for example, a Teflon-coated magnet. In some aspects, the magnetically-responsive object may comprise a capsule containing a magnetically-responsive member. The capsule may comprise a polymer.

In accordance with various aspects of the disclosure, a method of delivering micronized dry powder particles to a patient may include rotating a magnet exterior to a chamber to create a magnetic field that causes responsive movement of at least one magnetically-responsive object coated with micronized dry powder particles and contained in the chamber, deaggregates the micronized dry powder particles from the magnetically-responsive object, and aerosolizes the deaggregated particles in the chamber. The method further includes directing a flow of air including the aerosolized particles from the chamber to an outflow member.

In some aspects, the rotating step begins in response to patient activation, which may include inhalation at a mouthpiece coupled with an outflow member of the container.

DETAILED DESCRIPTION

Figure 1:
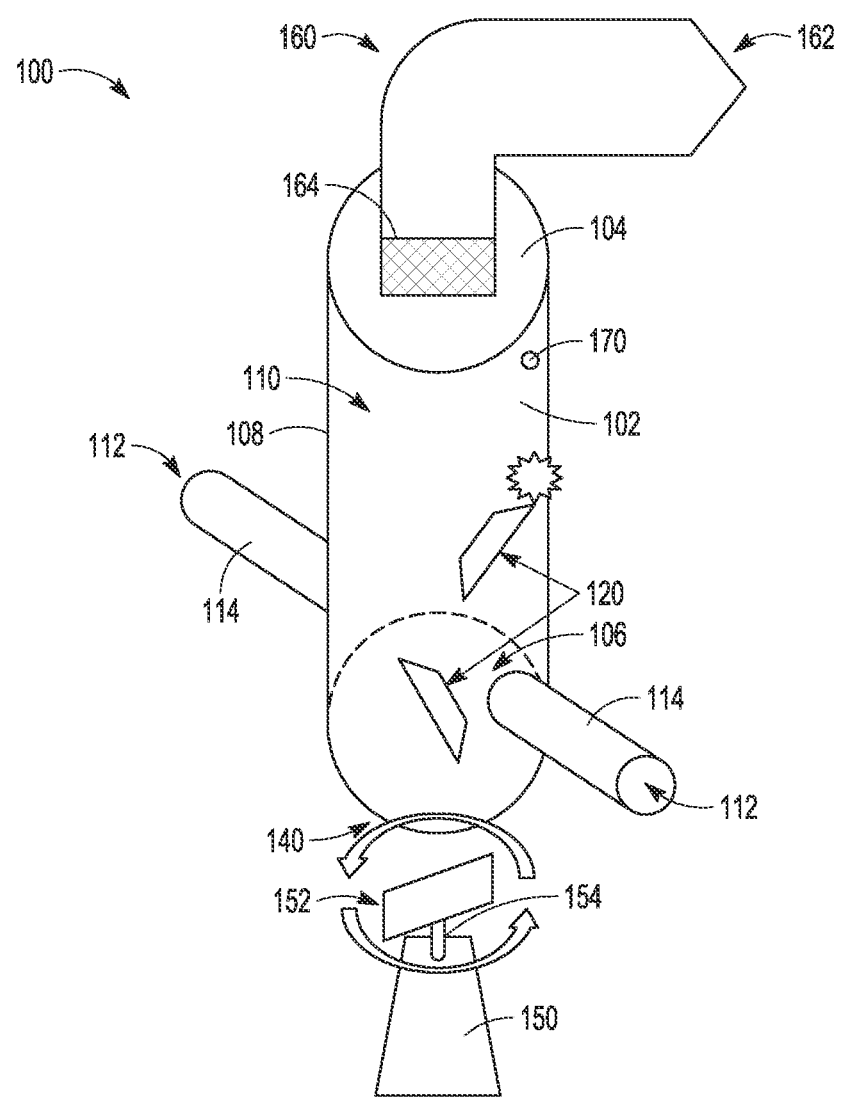
FIG. 1 is a perspective view of an exemplary dry powder nebulizer in accordance with various aspects of the disclosure.
Figure 2:
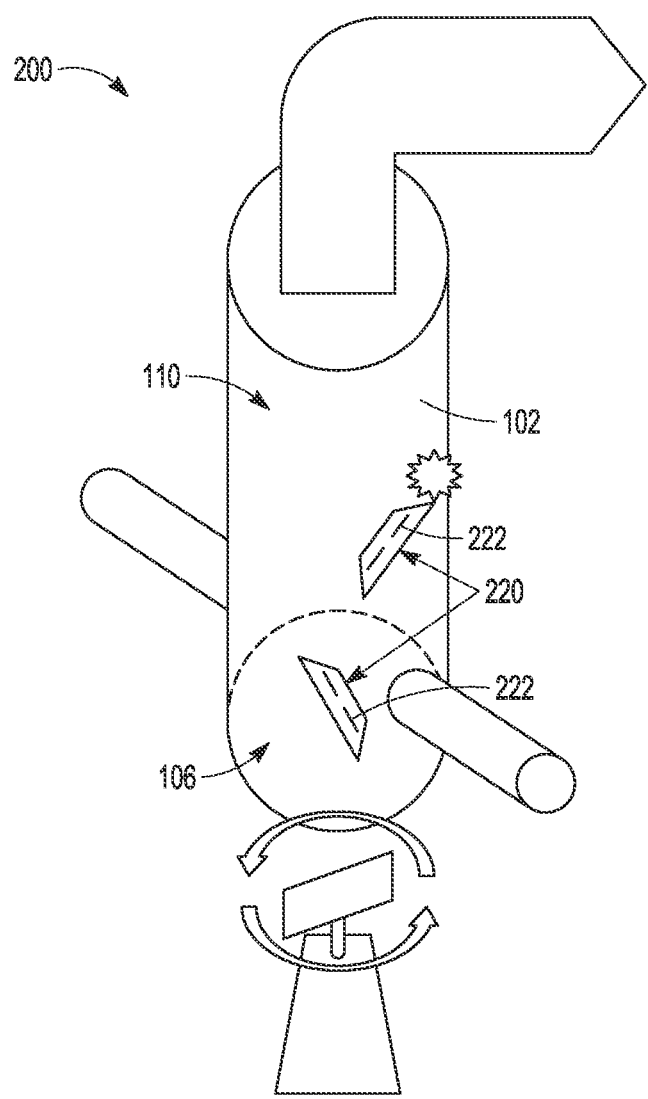
FIG. 2 is a perspective view of an exemplary dry powder nebulizer in accordance with various aspects of the disclosure.

FIGS. 1 and 2 illustrate a diagrammatic perspective view of a drug delivery device comprising an exemplary dry powder nebulizer assembly 100 according to various aspects of the disclosure. The dry powder nebulizer assembly 100 includes a container 102 having a top wall 104, a bottom wall 106, and at least one side wall 108 extending between the top and bottom walls 104, 106. The top wall 104, bottom wall 106, and side wall 108 cooperate to delimit a dosing chamber 110. According to various aspects, the bottom wall 106 may be pounded out so as to form an uneven, bumpy inner bottom surface of the dosing chamber 110. The effect of the uneven bottom surface is discussed in more detail below.

According to some aspects, the container 102 may comprise a container such as, for example, a cylindrical aluminum canister. It should be appreciated that the container may comprise a metal, a polymer, or a combination thereof as long as it is not a paramagnetic material. In some aspects, a low static material that does not triboelectrify may be desirable. In some embodiments, the cylindrical canister may measure about 1.5 to 3 inches in height, for example, about 2.25 inches. In some aspects, the cylindrical canister may taper from the bottom wall 106 to top wall 104. For example, in one exemplary embodiment, the canister may taper from a diameter of about 0.875 inches at the bottom wall 106 to about 0.7 inches at the top wall 104. According to various embodiments, the diameter at the bottom wall 106 of the canister may range from 0.7 to 1 inch, and the diameter at the top wall 104 of the canister may range from about 0.5 to 0.8 inches. It should be appreciated that these ranges are exemplary only and may be lesser or greater depending on the user's desired parameters.

The container 102 may include one or more air inlets 112 in the side wall 108. According to some aspects, the container 102 may include two air inlets 112 provided via hollow shafts 114 disposed at opposite sides of the container 102 relative to one another. The shafts 114 extend outward from the container 102 in directions opposite to one another.

The container 102 contains a magnetically responsive object. Referring to FIG. 1, according to some aspects, the container 102 may contain at least one miniature magnet 120 in the dosing chamber 110. The at least one magnet 120 may comprise, for example, a plurality of micron-sized, polymer-coated magnets or magnetically-responsive beads. The number, weight, and size of magnets 120 may vary according to the size of the container 102, the desired dosing, and other design parameters. In some aspects, the magnets 120 may range from about 300 µg to about 1 mg in weight. In some embodiments, the magnets 120 may have a length from about 0.35 to 0.4 inches, a width of about 0.1 to 0.15 inches, and a thickness of about 0.1 to 0.15 inches. For example, the magnets 120 may have a length of about 0.375 inches, a width of about 0.125 inches, and a thickness of about 0.125 inches. It should be appreciated that the aforementioned ranges are exemplary only and may be lesser or greater depending on the user's desired parameters. According to some aspects, for example, the magnet(s) or bead(s) may comprise a Teflon-coated magnet(s) or bead(s). Further, the polymer-coated magnet(s) or bead(s) includes a desired drug coated thereon.

Referring now to FIG. 2, in some aspects, a nebulizer assembly may include a container 102 containing at least one capsule 220. In some aspects, the capsule 220 may comprise a polymer or a polymer coating, such as, for example, Teflon. Each capsule 220 contains a pre-measured amount of drug powder and at least one miniature magnet 222. In some aspects, each magnet 222 may comprise a stir bar or a neodymium magnet, for example. The magnet(s) 222 help to weigh down the capsule(s) 220 such that gravity keeps the capsule(s) toward the bottom wall 106 of the container 102 in the dosing chamber 110.

Referring again to FIG. 1, the nebulizer assembly 100 further includes a motor 150 external to the container 102. The motor 150 may comprise a small conventional rotational motor, such as for example a motor used in toys and the like. The motor 150 may have a lower power requirement such that one or more small button-type batteries, for example three hearing air type batteries, may be employed as a power source and may be contained in a housing associated with the motor. In some embodiments, the motor may operate at approximately 1800 to 2200 revolutions per minute. According to some aspects, the motor 150 may be powered by an ac power source.

The motor 150 may include a magnet 152 coupled with the output shaft 154 of the motor 150 so as to rotate therewith. The magnet 152 may comprise a rare earth magnet such as, for example, a neodymium magnet. In some aspects, the magnet 152 may be cylindrical; however, it should be understood that other shapes of magnets may be used depending on the user's desired parameters. It should be appreciate that any other types of magnets and/or magnetic materials may be utilized. Generally, a stronger external magnet 152 may be used if the internal magnets 120, 222 are weaker, and a weaker external magnet 152 may be used if the internal magnets 120, 222 are stronger. The size of the magnet may vary based on the need to create a magnetic field sufficient to influence movement of the magnets 120 or capsules 220 contained in the dosing chamber 110 of the container 102 when the magnet 152 is placed in proximal relation to an outer surface 140 of the bottom wall 106 of the container 102. According to various aspects, the nebulizer 100 may be activated when the motor 150 is activated via a patient-operated control switch (not shown). In some aspects, the nebulizer 100 may be activated when a patient inhales at the mouthpiece, as would be understood by persons skilled in the art.

The nebulizer assembly 100 further includes an outflow member 160 for delivering air containing aerosolized drug particles to a patient. In some aspects, the outflow member 160 may comprise a conduit, for example, rubber tubing coupled at one end to the top wall 104 of the container 102 in an airtight relationship. A second, opposite end of the outflow member 160 may form a mouthpiece 162 configured for insertion into a patient's mouth during an inhalation procedure. In some aspects, a separate mouthpiece (not shown) may be coupled with the outflow member 160. In various aspects, the outflow member 160 and/or mouthpiece may be removable from the assembly 100 and/or disposable. In some aspects, the tubing may measure approximately 0.8 inches in diameter and 6 inches length.

The outflow member 160 may contain a filtering member 164 such as, for example, a mesh for preventing undesired particulate from exiting the nebulizer assembly 100 via the mouthpiece 162 and entering a patient's airways. According to some embodiments, the filtering member 164 may comprise non-paramagnetic wiring woven and incorporated in the outflow member 160 to create a mesh to prevent unwanted particulate from entering the airways. The container 102 may include an inlet hole 170 for dilution air during breathing/inhalation by the patient.

Figure 3:
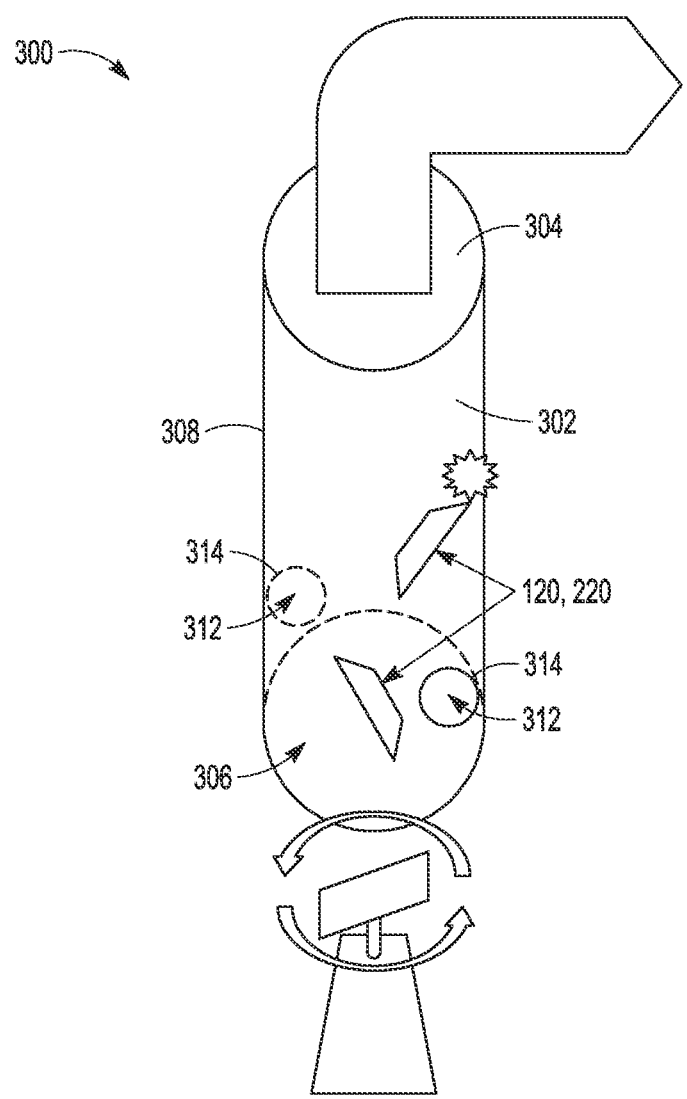
FIG. 3 is a perspective view of an exemplary dry powder nebulizer in accordance with various aspects of the disclosure.

FIG. 3 illustrates a perspective view of an exemplary dry powder nebulizer 300 according to the disclosure. The nebulizer 300 is similar to the exemplary nebulizer 100 described above. However, in the nebulizer 300, the airflow inlets 312 comprise holes 314 in the side wall 308 of the container 302. FIG. 3 illustrates the holes 314 on opposing regions of the side wall 308 proximate a bottom wall 306 of the container 302. However, it should be appreciated that the holes 314 may be disposed at other locations along the side wall 308 between the bottom wall 306 and a top wall 304.

In operation, the nebulizer 100, 300 may be activated via patient-operated switch that activates the motor. Additionally or alternatively, the nebulizer may be activated when a patient inhales at the mouthpiece, as would be understood by persons skilled in the art. Once the nebulizer 100, 300 is activated, the motor and associated magnet turn and generate a magnetic field. The substantially constant revolution and resulting magnetic field cause the magnets or capsules in the dosing chamber to continuously collide with the side wall of the dosing chamber. The drug-coated magnet(s) 120 or capsule(s) 220 containing drug powder displays a chaotic movement directed by the influence of changing magnetic fields induced by the external magnet/motor and the internal shape of the dosing/holding chamber that causes collisions and forces of deaggregation for the drug-coated internal magnet/bead. This force disperses the deaggregated drug into a "cloud" which can then be inhaled by the patient over a set period of time.

The uneven inner surface of the bottom wall of the container facilitates the collisions between the magnets or capsules and the side wall. The airflow inlets extending tangentially from the side wall of the container proximal the bottom wall help to create an upward cyclonic push of air during activation of the motor. Such upward cyclonic push may improve the aerosolization of the drug powders and reduce the amount of drug which adheres to the inner surface of the side wall of the container, thereby improving efficiency of the nebulizer.

The dosing chamber may include an inlet hole for dilution air during breathing/inhalation by the patient. The inhalation aerosol may be directed from the dosing chamber to the mouthpiece via the outflow member or other conduit. According to various aspects, the nebulizer may include a mesh, screen, filter, or the like positioned in the path of airflow from the dosing chamber to the mouthpiece so as to prevent the magnet(s) or bead(s) from leaving the chamber and reaching the patient.

Regarding exemplary embodiments including capsules contained in the dosing chamber of the container, the capsules may contain a premeasured amount of micronized drug powder encapsulated therein. The capsules include at least one hole sized such that once the nebulizer is activated, drug can be released via the at least one hole as the capsules are moved about and collide with the side wall and/or with one another in the dosing chamber.

In some aspects, the capsule may be pierced to form one or more holes immediately prior to use. For example, the ends of the capsule can be pierced with 1-3 pin-sized holes on one or both sides. In some aspects, the capsule may have as few as one hole and as many as six or more holes, for example. It should be appreciated that the number and size of the holes may vary depending on the desired performance of the nebulizer. Persons skilled in the art would understand that the exemplary nebulizers may include a piercer (not shown) associated therewith. A user may squeeze a region of the nebulizer to cause the piercer to pierce the capsule as would be understood by persons skilled in the art.

Regarding exemplary embodiments including a drug-coated micron-sized magnet or magnetically-responsive bead, drug powders may be loaded onto the micron-sized carrier magnets or bead, for example, by affixing a small spherical canister with loose drug and magnets/beads inside to a slow rotating motor (e.g., as would be seen in a low-tech tape recorder). The magnets/beads are thereby coated with multiple layers of drug powder. It should be appreciated that any method of coating magnets/beads is contemplated by and consistent with the present disclosure.

It should be appreciated that nebulizers consistent with the present disclosure may provide customized medication delivery for patients. It should also be appreciated that any medication, drug, therapeutic, or other treatment particle desired to be delivered to a patient's airways is contemplated by the present disclosure. For example, the amounts (0.5 mg to several milligrams) and types of drug powders (antibiotics, long-acting beta agonists, steroids, immunosuppressives, etc.) could potentially be varied for patients and compounded based on standardized modeling of performance. By doing so, the nebulizer can be tailored to a patient's individual needs. For example, patients might need several antibiotics for treatment of cystic fibrosis, etc., and nebulizers consistent with the present disclosure might be able to provide all of them to a patient in one treatment. It should be appreciated that treatments can also be adjusted as the patient's needs change by simply compounding the capsules/carriers differently.

It should be appreciated that nebulizers consistent with the present disclosure may provide one or more advantages such as increased efficiency, improved stabilization, ease of use, predictable delivery of medication, and reproducible delivery. Regarding increased efficiency, a substantial amount of drug may be delivered over seconds (as compared to 15-20 minutes with a traditional nebulizer) without the need of a bulky power source. Dry powder formulations may provide improved stabilization because such medications are less likely to degrade and dosing can be easily adjusted for each patient.

It should be appreciated that nebulizers of the present disclosure do not require the coordination needed with conventional metered dose inhalers, nor do they require the inspiratory capacity needed to sufficiently activate a traditional dry powder inhaler. The power source used to activate the motor may comprise three conventionally-available hearing aid batteries, and the overall size of the device may be small enough to fit in a purse or small carrying device.

It should be appreciated that nebulizers of the present disclosure may deliver a predictable amount of micronized drug to the "in vitro deep lung" which suggests a patient will receive his/her intended dose in the desired portion of their airway system. Delivery to the patient may also be reproducible despite variations in inspiratory capacity. Tests have shown that the dispersion of the micronized powders remains substantially consistent for airflow rates at 30 L/min and 60 L/min. Therefore, as a patient's lung function changes from day to day (depending on the control of their condition, illness, fatigue, etc.) the same dose can be delivered.

Dispersion studies have been performed using a Next Generation Impactor (NGI), a device designed to model particle deposition in the human airways. The NGI consists of several components to replicate the mouth, neck, and various sub-fractions of the lung. Tracking how the drug disperses in the various compartments is necessary to predict the proportion of drug swallowed versus inhaled (a measure to predict side effects and systemic absorption through the gastrointestinal tract), drug remaining in the device, and drug which reached the target—the deep lung. Data analysis includes a series of efficiency measures (fine particle fraction (FPF), respiratory fraction (RF), and the fine particle dose (FPD)). These parameters are applicable when estimating the potential costs associated with the device as well as dosing limitations and side effects.

The device has shown to be more efficient (relative to other devices on the market) and consistent in the delivery of our model drug, ciprofloxacin, at a relatively low inspiratory flow rate of 30 L/min for powder based systems. The majority of the drug that enters the body reaches the deep lung, which is a desirable trait when considering targeted drug therapy. Further, upon observation, our device seems to be rather consistent in delivery despite positioning changes. Our inhaler also has the ability to deliver large doses of drug over 15-30 seconds at 30 L/min, while maintaining a significantly improved efficiency compared to those on the market. This may have profound applications in a number of diseases. For example, fungal infections of the lung, especially in neutropenic patients who typically require fungicidal activity.

Fungal infections of the lung most commonly involve *Candida* and *Aspergillus* organisms. Many of these organisms have become resistant to the anti-fungal azole class, and neutropenic patients often require prolonged hospitalization and intravenous formulations of amphotericin B or drugs within the echinocandin class, leading to skyrocketing healthcare costs. In addition to these organisms, other pathogens such as *Cryptococcus* continue to surface and pose mortality threats as well as increased costs. Thus, formulations of amphotericin B and/or caspofungin (or another from the echinocandin class) complex for use in our device would have significant advantages in therapeutics. This novel and effective method to effectively treat primary fungal infections may achieve substantially improved patient outcomes (mortality) and cost-effectiveness.

In addition to fungal infections, this technology has the potential to target other disease states of the lung where large quantities of drug are desired but where the patient lacks the ability to utilize other current methods. Moreover, delivery of high doses of drugs delivered to the lung for the purposes of systemic absorption is an attractive application and embodiment of the technology.

Example

METHOD: Ciprofloxacin drug particles were jet-milled to micronized drug particles and loaded onto micron-sized, polymer coated magnets using a custom made tumbling apparatus.

Trials to establish dispersion patterns were conducted using 2 drug-loaded magnets. Payload capability data was generated using 4 drug-coated magnets.

A custom-made nebulizer device was assembled and comprised a neodynium magnet fixed upon a handheld, patient-operated, motor-driven rotating element external to a chamber where the drug-coated magnets were held. Upon activation of the motor, the rotation of the external magnet created a dynamic movement of the drug-coated magnets through magnetic field changes within the chamber (created by the rotating external magnet), which led to the production of an aerosolized drug cloud in the container. The outflow conduit of the container was fluidly coupled to a model airway system so that the aerosolized drug was then able to be drawn into the model airway system to assess performance.

All studies were conducted using a Next Generation Impactor (NGI®) at 30 L/min for 30 seconds. The NGI® is an in vitro model of the human upper airways and lungs designed to predict particle deposition in the human airways. Concentrations in each component of the device and NGI were determined via UV absorbance at 480 nm, from which aerosol distribution patterns were calculated. Typical efficiency and performance measures, fine-particle fraction (FPF), respirable fraction (RF), and fine-particle dose (FPO), were subsequently calculated.

As used throughout this disclosure, fine-particle fraction refers to the amount (%) of drug delivered to the deep lung (trays 3-8 of the NGI) relative to the amount of drug delivered to the body (mouth, throat, lung (i.e., mouth, ps, and trays 1-8)). The respirable fraction (RF) refers to the amount (%) of drug delivered to the deep lung (trays 3-8 of the NGI) relative to the starting dose. The fine particle density (FPO) refers to the amount of drug (micrograms) which penetrate the deep lung (trays 3-8 of the NGI).

Figure 4:
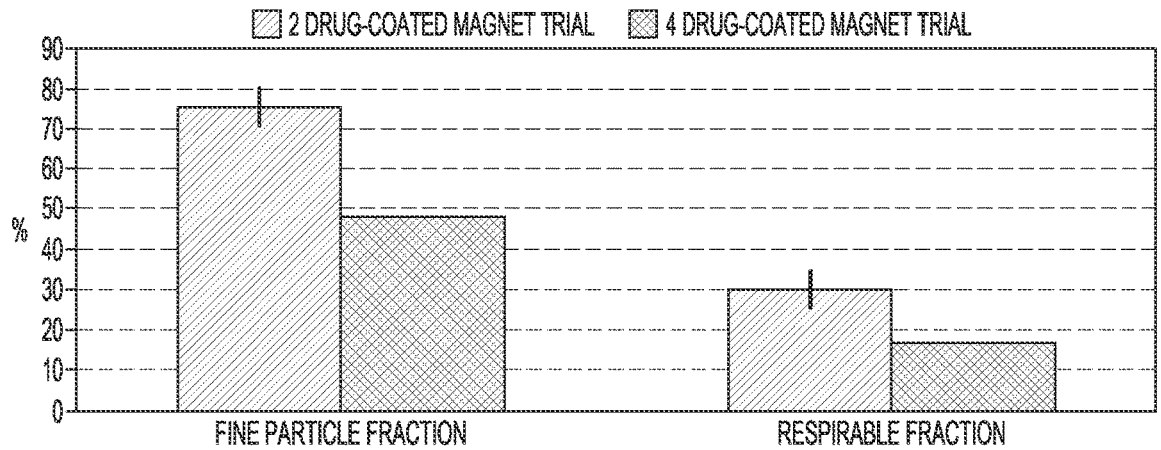
FIG. 4 is a graph illustrating performance measures of an exemplary nebulizer using ciprofloxacin drug particles.

RESULTS: Using 2 drug-coated magnets, an average fine-particle fraction (FPF) and respirable fraction (RF) of 75% and 29%, respectively, was achieved and an average dose of 950 micrograms was delivered to the "in vitro deep lung" of the NGI. FIG. 4 illustrates the performance measures of a device using ciprofloxacin. Fine particle fraction is the proportion of drug that reached the "in vitro deep lung" relative to the total amount which entered the NGI. Respirable fraction is the proportion of drug that reached the "in vitro deep lung" relative to the full dose. That is, respirable fraction accounts for drug which remained in the nebulizer device and NGI.

Figure 5:
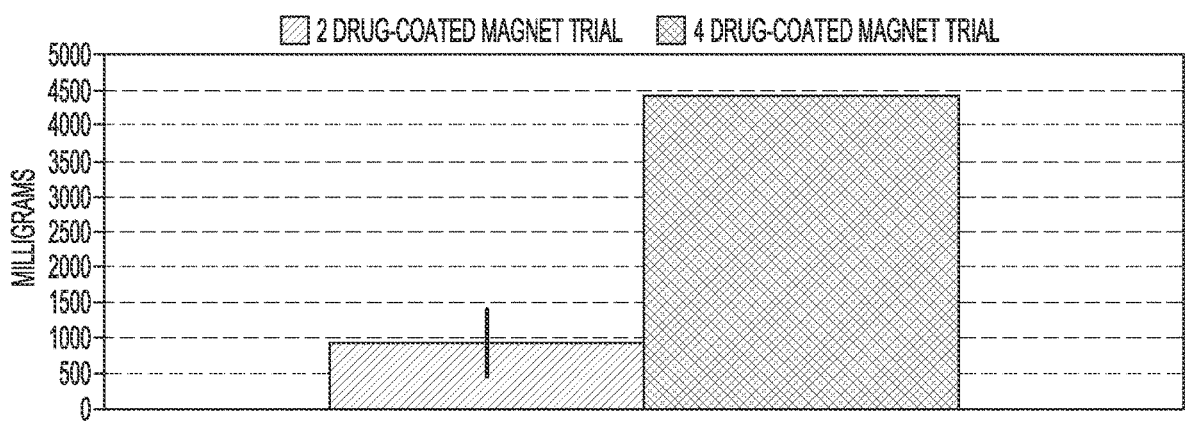
FIG. 5 is a graph illustrating the quantity (mg) of ciprofloxacin delivered to the "in vitro deep lung" by an exemplary nebulizer.
Figure 6:
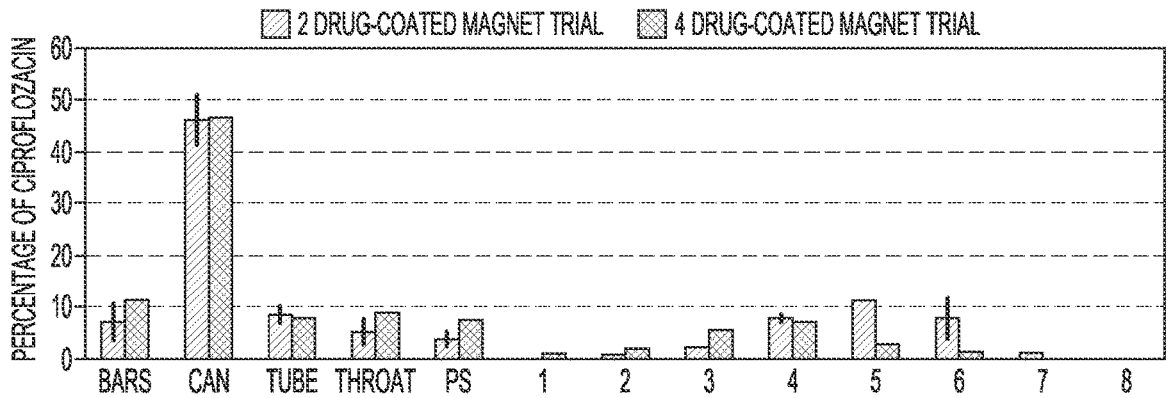
FIG. 6 is a graph illustrating the percentage of ciprofloxacin distributed in various components of a model airway system and an exemplary nebulizer.

When 4 drug-coated magnets were employed, greater than 4.4 milligrams of ciprofloxacin was delivered to the "in vitro deep lung" of the NGI, however the overall efficiency of the set-up was reduced (FPF=48%, RF=17%), as illustrated in FIGS. 4 and 5. FIG. 6 illustrates the percentage of ciprofloxacin distributed in various components of the model airway system (i.e., NGI) and the nebulizer device.

It can be concluded that the low inspiratory capacity needed to generate the deposition patterns observed may be advantageous when considering patient populations who have compromised lung function. The high payload capabilities present opportunities to exploit new targeted therapeutic strategies.

It is noted that, as used in this specification and the appended claims, the singular forms "a," "an," and "the" include plural referents unless otherwise expressly and unequivocally limited to one referent. Thus, for example, reference to "a nebulizer" includes two or more different nebulizers. As used herein, the term "include" and its grammatical variants are intended to be non-limiting, such that the recitation of items in a list is not to the exclusion of other like items that can be substituted or other items that can be added to the listed items.

It will be apparent to those skilled in the art that various modifications and variations can be made to the systems and methods of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A device comprising:
   a container defining a chamber, the chamber containing at least one magnetically-responsive object and micronized powder particles, wherein the at least one magnetically-responsive object moves due to changes in a magnetic field within the chamber;
   an outflow member configured to direct an airflow from the chamber, and
   a motor;
   wherein movement of the motor causes a change in the magnetic field that causes a responsive movement of the at least one magnetically-responsive object that deaggregates at least a portion of the micronized powder particles into the airflow.

2. The device of claim 1, further comprises a magnet coupled to the motor, wherein the movement of the motor acts to move the magnet, and wherein movement of the magnet causes the change in the magnetic field.

3. The device of claim 1, wherein the at least one magnetically-responsive object comprises a magnet.

4. The device of claim 1, wherein the outflow member includes a mouthpiece in fluid communication with the chamber.

5. The device of claim 1, further comprising at least one air inlet to allow air into the chamber.

6. The device of claim 1, wherein the responsive movement of the at least one magnetically-responsive object deaggregates and at least partially aerosolizes the micronized powder particles.

7. The device of claim 1, wherein the dose of micronized powder particles are coated on the at least one magnetically-responsive object, wherein the responsive movement of the at least one magnetically responsive object causes at least the portion of the micronized powder particles to deaggregate from the at least one magnetically responsive object into the airflow.

8. The device of claim 1, wherein the responsive movement of the at least one magnetically responsive object causes the at least one magnetically-responsive object to collide with a structure in the chamber to deaggregate at least the portion of the micronized powder particles from the magnetically-responsive object.

9. The device of claim 1, wherein the micronized powder particles comprise micronized drug particles.

10. The device of claim 9, wherein the micronized drug particles comprise at least one of an antibiotic, a long-acting beta agonist, a steroid, and an immunosuppressive.

11. A method comprising:
  providing or receiving a powder delivery device comprising a container defining a chamber containing at least one magnetically-responsive object and micronized powder particles, a motor, and an outflow conduit in fluid communication with the chamber;
  moving the motor, which causes a change in a magnetic field within the chamber, wherein the change in the magnetic field causes a responsive movement of the at least one magnetically-responsive object that deaggregates at least a portion of the micronized powder particles within the chamber; and
  directing an airflow of air including the deaggregated micronized powder particles out of the chamber through the outflow conduit.

12. The method of claim 11, wherein the powder deliver device further comprises a magnet, wherein the magnet is coupled to the motor so that the moving of the motor moves the magnet, wherein magnetic attraction between the magnet and the at least one magnetically-responsive object creates the change in the magnetic field.

13. The method of claim 11, wherein the moving of the motor begins in response to activation by a user.

14. The method of claim 13, wherein the activation comprises inhalation by the user through the outflow conduit.

15. The method of claim 11, wherein the at least one magnetically-responsive object comprises a magnet.

16. The method of claim 11, wherein the responsive movement of the at least one magnetically-responsive object deaggregates and at least partially aerosolizes the micronized powder particles.

17. The method of claim 11, wherein the dose of micronized powder particles are coated on the at least one magnetically-responsive object, wherein the responsive movement of the at least one magnetically responsive object causes at least the portion of the micronized powder particles to deaggregate from the at least one magnetically responsive object.

18. The method of claim 11, wherein the responsive movement of the at least one magnetically responsive object causes the at least one magnetically-responsive object to collide with a structure in the chamber to deaggregate at least the portion of the micronized powder particles from the magnetically-responsive object.

19. The method of claim 11, wherein the micronized powder particles comprise micronized drug particles.

20. The method of claim 19, wherein the micronized drug particles comprise at least one of an antibiotic, a long-acting beta agonist, a steroid, and an immunosuppressive.

* * * * *